(12) United States Patent
Yalcin et al.

(10) Patent No.: US 11,998,911 B2
(45) Date of Patent: Jun. 4, 2024

(54) MICROFLUIDIC THROMBOELASTOMETRY INSTRUMENT

(71) Applicant: KOC UNIVERSITESI, Istanbul (TR)

(72) Inventors: Ozlem Yalcin, Istanbul (TR); Ahmet Erten, Istanbul (TR); Melikhan Tanyeri, Istanbul (TR)

(73) Assignee: KOC UNIVERSITESI, Istanbul (TR)

( * ) Notice: Subject to any disclaimer, the term of this patent is extended or adjusted under 35 U.S.C. 154(b) by 675 days.

(21) Appl. No.: 17/260,822

(22) PCT Filed: Jul. 29, 2018

(86) PCT No.: PCT/TR2018/050405
§ 371 (c)(1),
(2) Date: Jan. 15, 2021

(87) PCT Pub. No.: WO2020/027741
PCT Pub. Date: Feb. 6, 2020

(65) Prior Publication Data
US 2021/0268497 A1    Sep. 2, 2021

(51) Int. Cl.
*G01N 11/04*    (2006.01)
*B01L 3/00*    (2006.01)
*G01N 33/49*    (2006.01)

(52) U.S. Cl.
CPC .......... *B01L 3/50273* (2013.01); *G01N 11/04* (2013.01); *G01N 33/4905* (2013.01);
(Continued)

(58) Field of Classification Search
CPC ..... B01L 2200/0652; B01L 2300/0832; B01L 2300/0877; B01L 2300/123;
(Continued)

(56) References Cited

U.S. PATENT DOCUMENTS 10,114,031 B2 * 10/2018 Di Tullio ........... G01N 27/4166
10,725,018 B2 *  7/2020 Nadkarni .......... B01L 3/502715
(Continued)

FOREIGN PATENT DOCUMENTS

EP    2419217 A1 *  2/2012  .............. B01L 3/502
EP    3141900 A1     3/2017
(Continued)

*Primary Examiner* — Andre J Allen
(74) *Attorney, Agent, or Firm* — Bayramoglu Law Offices LLC

(57) ABSTRACT

A microfluid thromboelastometry instrument for analyzing a viscosity of a sample fluid is provided. The microfluid thromboelastometry instrument includes a cartridge for measuring changes in the viscosity of a fluid, the cartridge includes an inlet and an outlet, wherein a flow of the fluid is provided through the cartridge between the inlet and the outlet. The cartridge includes at least one micro-pillar having at least one first position, the at least one micro-pillar is capable of bending with a fluid flow, and an amount of bending increases as the viscosity of the fluid increasing and restores to the at least one first position of the at least one micro-pillars in response to viscosity decrease of the fluid. The micro-pillar is fixed to the surface of the cartridge from the root and has a free distal extremity. A displacement of the micro-pillar distal extremity relative to the micro-pillar root is monitored.

32 Claims, 9 Drawing Sheets

(52) U.S. Cl.
CPC .............. *B01L 2300/0832* (2013.01); *B01L 2300/0877* (2013.01); *B01L 2400/086* (2013.01)

(58) Field of Classification Search
CPC ....... B01L 2400/0478; B01L 2400/086; B01L 3/50273; B01L 3/502761; G01N 11/02; G01N 11/04; G01N 2035/00148; G01N 33/4905; A61F 2/2412; A61F 2/2418; A61F 2002/8483; A61F 2002/9528; A61F 2250/0059; A61F 2250/006
See application file for complete search history.

(56) References Cited

U.S. PATENT DOCUMENTS

| | | | |
|---|---|---|---|
| 10,746,750 B2 * | 8/2020 | Schubert | B01L 3/502 |
| 11,327,069 B2 * | 5/2022 | McCluskey | G01N 33/86 |
| 2005/0136541 A1 * | 6/2005 | De Haan | B01L 3/502 |
| | | | 422/536 |
| 2008/0014589 A1 * | 1/2008 | Link | B01J 19/0093 |
| | | | 137/896 |
| 2008/0071487 A1 | 3/2008 | Zeng et al. | |
| 2008/0261261 A1 | 10/2008 | Grimes et al. | |
| 2013/0183659 A1 * | 7/2013 | Link | C12N 15/1068 |
| | | | 435/6.12 |
| 2016/0069913 A1 | 3/2016 | Bakhru et al. | |
| 2016/0091483 A1 * | 3/2016 | McCluskey | B01L 3/567 |
| | | | 422/501 |
| 2016/0091517 A1 | 3/2016 | Gorin et al. | |
| 2017/0189903 A1 | 7/2017 | Delmenico et al. | |
| 2017/0370905 A1 | 12/2017 | Rousseau et al. | |

FOREIGN PATENT DOCUMENTS

| | | | |
|---|---|---|---|
| EP | 3058367 B1 * | 1/2019 | .......... B01L 3/50273 |
| WO | 9512117 A1 | 5/1995 | |
| WO | 2010038230 A1 | 4/2010 | |

* cited by examiner

MICROFLUIDIC THROMBOELASTOMETRY INSTRUMENT

CROSS REFERENCE TO THE RELATED APPLICATIONS

This application is the national stage entry of International Application No. PCT/TR2018/050405, filed on Jul. 29, 2018, the entire contents of which are incorporated herein by reference.

TECHNICAL FIELD

The present invention relates to an apparatus for analyzing the viscosity of a sample fluid. In particular, the present invention concerns a method and a device for determining viscosity change with time for conducting coagulation assays.

BACKGROUND

Coagulation is the procedure by which blood changes its state from a fluid to a gel for generating a blood clot. It possibly brings about hemostasis, the end of blood loss through a harmed vessel. The mechanism of coagulation involves activation, adhesion, and aggregation of platelets along with deposition and maturation of fibrin.

After William Harvey's definition of blood circulation in the circulatory system as a continuous closed circuit, it was understood that the blood must remain in the vascular system in order for circulation to continue. The fluid retention and circulatory function to prevent coagulation of blood tissue are achieved by the critical balance of anticoagulant and thrombolytic-fibrinolytic mechanisms. Hemostasis is a precise physiological process for stopping the bleeding, repairing vascular injury without impairing blood flow. After vascular injury, a series of complex reactions occur between vascular elements, blood cells and plasma proteins resulting in a controlled hemostasis or thrombus development. Blood vessel injuries, high shear stress and blood contact with the conflicting surfaces commence hemostatic processes.

Extrinsic (through tissue factor) and intrinsic pathways (contact with non-physiological surfaces) are important in the activation of the coagulation system, and these two pathways coalesce in factor X, which is called the common pathway. The physiological activation of the coagulation takes place almost entirely via tissue factor (TF) and activation of the extrinsic pathway is completed by the activation of TF.

The contact of TF and factor VII leads to the formation of an active complex. This complex also activates FX. The presence of phospholipids and calcium ions cause more effective formation. The initiation of the intrinsic pathway is related to the surface of the blood, particularly if the surface is negatively charged, it triggers the complex interaction of some proteins. In the presence of FXIIa activated by kallikrein, kallikrein is formed by the action of high molecular weight kininogen on prekallikrein. FXIIa, which is also activated by kallikrein, activates FXI. FXIa activates FIX and FIXa activates FX. All steps in the cascade require calcium and are phospholipid-dependent.

Contact activation plays a very significant role in contact with nonphysiological surfaces. The next step after activation of FX in coagulation cascade is prothrombin activation. Prothrombin is converted to thrombin with the help of FXa and FVA complex. The resulting thrombin also converts fibrinogen to fibrin. After the effect of thrombin, FXIII is activated in a calcium-dependent reaction almost simultaneously. FXIIIa provides cross-linking between the fibrin monomers. It also provides cross-linking between the clot and some other proteins. The strength and stability of the clot, in other words its physical properties, determines the primary function of the hemostasis which is the mechanical capacity of the hemostasis.

The clot as a damage control tool is actually a temporary interruption that slowly dissolves while recovery of the vessel damage is ongoing. Fibrinolysis is a phenomenon that removes fibrin deposits, improves circulation in blood vessels and facilitates the repair process following tissue injury. For the fibrinolytic system to be active, the plasminogen needs to be converted to plasmin which is a proteolytic enzyme. It breaks down the fibrin mesh and produces fibrin degradation products of different sizes. The smallest of these products is the d-dimer and has diagnostic significance. Plasminogen to plasmin translocation is done by intrinsic and extrinsic activator systems and by exogenous pathways. Plasmid formed by the intrinsic activator system is only 15% of total fibrinolytic activity.

Some coagulation analyze devices can be used in cardiopulmonary bypass surgery, trauma, liver transplantation, obstetric, orthopedics and hemophilia. These devices are essential and widely used to respond quickly in the diagnosis of coagulopathies.

Thromboelastography (TEG) and tromboelastometry (TEM) based coagulation analyzers have been used to quickly determine the origins of possible coagulopathies by examining the blood viscoelastic properties and stages of blood coagulation (hemostasis). These devices are able to quickly distinguish between coagulopathy and bleeding during surgical operations. In clinic, TEM and TEG coagulation devices are widely used in cardio-pulmonary bypass surgery, trauma, liver transplantation, obstetrics, orthopedia and haemophilia and can respond rapidly upon the diagnosis of coagulopathies. Differential diagnostics, target therapy and therapy monitoring performed with the help of modified TEG systems that have been developed in the recent years result in better patient treatments. In addition, the effects of target therapy can be measured immediately with these devices; thus the risk of complications from the treatment is minimized through monitoring the effects on the patient after therapy. The implementation of transfusion using the test results of these devices enables more accurate transfusions of the components (blood products, anticoagulant and protamines, haemostatic and antifibrinolytic drugs) as well as the avoidance of unnecessary transfusions. Thus, coagulation analyzers provide fast, efficient and cost-effective therapy in clinical cases. These types of equipment are not preferred due to their high cost.

The attempts made in the state of the art to alleviate the problems associated with coagulation analyze devices are described in the following patents.

U.S. application Ser. No. 15/465,490 discloses a sample testing cartridge usable to perform a variety of tests on a viscoelastic sample, such hemostasis testing on a whole blood or blood component sample. The cartridge includes a sample processing portion that is in fluid communication with a sample retention structure. A suspension, such as a beam, arm, cantilever or similar structure supports or suspends the sample retention portion relative to the sample processing portion in a unitary structure. In this manner, the sample retention portion may be placed into dynamic excitation responsive to excitation of the cartridge and correspondingly dynamic, resonant excitation of the sample contained within the sample retention portion, while the sample processing portion remains fixed. Observation of the excited sample yields data indicative of hemostasis. The data may correspond to hemostasis parameters such as time to initial clot formation, rate of clot formation, maximum clot strength and degree of clot lysis.

International Appl. No. PCT/US94/10912 discloses an apparatus for conducting a variety of assays that are responsive to a change in the viscosity of a sample fluid and relates to methods of conducting such assays. In particular, the invention is related to the use of a cartridge for conducting one or more coagulation assays or, conversely, fibrinolysis assays. In particular, represents a conductivity sensor, sample flow channel, reagent chamber, sample chamber, sealable sample port, and a diaphragm which applies pressure to move the sample through the flow channels.

European Appl. No. EP3141900A1 discloses a cartridge for insertion into a device for measuring coagulation, comprising a housing in which a sample space is formed for receiving a sample fluid, and a vibrating element provided in the housing, which has an elongated housing connected to the housing and protruding therefrom into the sample space. Elastically bendable oscillating portion arranged at the free end of the vibrating portion and at least one adhesive surface defining the sample fluid sample contact portion, wherein the vibrating portion is formed rod-shaped with a particular rectangular or circular cross-sectional contour which is transverse to the longitudinal direction of the vibrating portion and transversely to the at least one swinging direction of a swinging section having a width corresponding to a maximum width of the sample contacting section in a ratio of at most 0.2, preferably at most 0.1.

U.S. application Ser. No. 15/535,696 discloses a determination method comprising the steps consisting of providing a reaction vessel containing a blood sample and a ferromagnetic ball placed on a raceway provided in the bottom of the reaction vessel, subjecting the ball to a magnetic field so as to move the ball along the raceway in an oscillatory motion, exposing the blood sample to an incident light beam, detecting a light beam transmitted through the reaction vessel and coming from the incident light beam in such a way as to provide a measurement signal, carrying out a first processing of the measurement signal in such a way as to provide a first signal representative of the variation of at least one physical quantity representative of the movement of the ball, carrying out a second processing of the measurement signal in such a way as to provide a second signal representative of the variation of at least one optical property of the blood sample, determining a first value of the coagulation time of the blood sample from the first signal, and determining a second value of the coagulation time of the blood sample from the second signal.

The present invention aims to develop a cost-effective, bedside global clotting (coagulation) diagnostic device for rapid evaluation of hemostatic function. The coagulation device preferably consists of a disposable cartridge unit comprising a core measurement unit and microfluidic channels, where the blood samples will be analyzed. Disposable microfluidic channels can be designed specifically for each test. The analyzer device quantitatively measures the coagulation starting time, clot formation time, maximum size to reach the time to clot, stiffness and elasticity of the clot, maximum clot firmness, stability and maximum lysis rate of clot through clotting curves. Targeted coagulation device based thromboelastogram (TEG) is different from existing systems because of its microfluidic design, low cost, and measurement capacity using a drop of blood. These features expand the use of such devices for different types of patients.

The object of the present invention is to provide a coagulation analysis device for the determination of blood coagulation phases with improved performance, low cost and reduced error rates in the test results.

SUMMARY

The present invention can primarily show the coagulation and fibrinolysis steps through clotting curves similar to TEM elastograms. The modified tests (heparinase, tissue factor, adding platelet blockers) can be used in healthy subjects and in different patient profiles. The movement of blood samples in microfluidic channels will be optically observed and specific disposable microfluidic channels will be designed for performing all measurements at a constant temperature.

The invention relates to taking blood samples from the patient to be injected into the cartridge unit without any preparation procedure. Clot formation and dissolution stages take place in cartridge unit and the viscoelastic properties of the blood are recorded with the measurement unit. While blood sample is driven back and forth in channel, it will interact with integrated elastic microstructures (micron-sized columns, valves, valve, etc.). In a variation of the present invention, blood flow can be introduced along a single direction instead of back and forth directions where sample volume is not limited. Subsequently the viscoelastic features of blood will be exactly and precisely determined by transferring this interaction to quantitative analysis. The association of the critical coagulation parameters obtained from time-dependent elasticity curves with coagulation disorders are examined and diagnostic/therapeutic use for data analysis algorithms are developed.

In summary, a device that allows data to be available for detailed quantitative analysis of the microstructure deformation based on the motion of the blood is developed for evaluation of patient-specific hemostasis mechanisms and treatment methods.

BRIEF DESCRIPTION OF THE DRAWINGS

Accompanying drawings are given solely for the purpose of exemplifying an apparatus for hemostasis testing, whose advantages over prior art were outlined above and will be explained in brief hereinafter.

The drawings are not meant to delimit the scope of protection as identified in the claims nor should they be referred to alone in an effort to interpret the scope identified in said claims without recourse to the technical disclosure in the description of the present invention.

REFERENCED PARTS LIST

10 Cartridge
11 Analyzing structure
12 Inlet
13 Outlet
14 Imaging unit
15 Micro-pillar
16 Mixing protrusion
17 Pumping unit
18 Microcontroller
19 Heating units
20 Power supply
21 Power plug
22 Screen
23 Microfluidic channel
24 Micro-pillar matrix
25 First micro-pillar field
26 Second micro-pillar field
27 Third micro-pillar field
28 Thromboelastography instrument
29 Left panel
30 Right panel
31 Back panel
32 Top panel Abbreviations used in the detailed description of the invention are listed below:
F) The force applied to the micro-pillar by the blood movement
E) Elastic modulus
D) Diameter of the micro-pillar
L) Height of the micro-pillar
x) Displacement of the micro-pillar tip relative to the root center

DETAILED DESCRIPTION OF THE EMBODIMENTS

Figure 1:
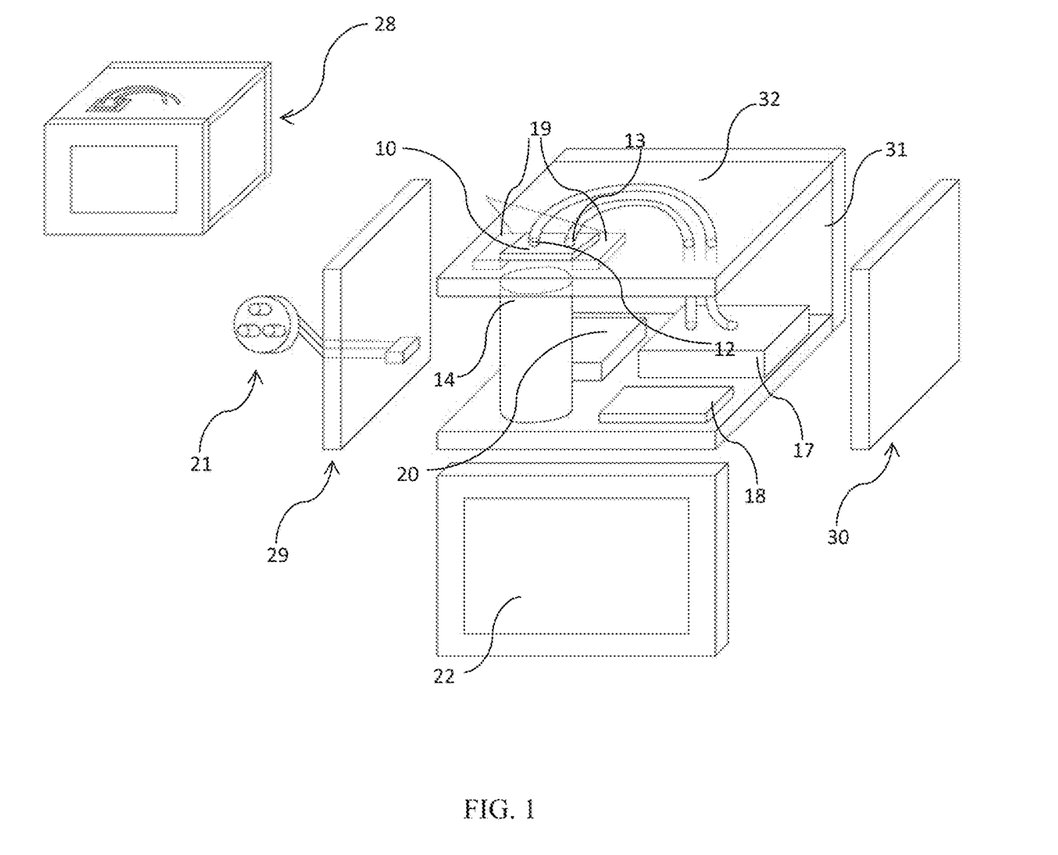
FIG. 1 is a general perspective view of a thromboelastography apparatus in accordance with this invention.

FIG. 1 demonstrates an exploded view of the whole system of a thromboelastography instrument (28) according to the invention. The thromboelastography instrument (28) comprises two main parts, a cartridge (10) and an analyzing structure (11). The analyzing structure (11) operates as a main computation unit and the cartridge (10) serves as a disposable dispenser containing microfluidic channels (23) for analysis of the blood sample. Primarily, the analyzing structure (11) consists of an imaging unit (14) to observe and process the deformations that structures in cartridge (10) are exposed to, a pumping unit (17) to accelerate the coagulation cascade by moving the blood sample injected into the cartridge back and forth through the microfluidic channels (23), heating units (19) to provide coagulation process corresponding to a patient's accurate body temperature and a microcontroller (18) to control all of system components. The analyzing structure (11) is a closed system comprising a left panel (29), a right panel (30), a back panel (31), a top panel (32), a power supply (20) and a power plug (21) as it can be seen from FIG. 1.

Figure 2:
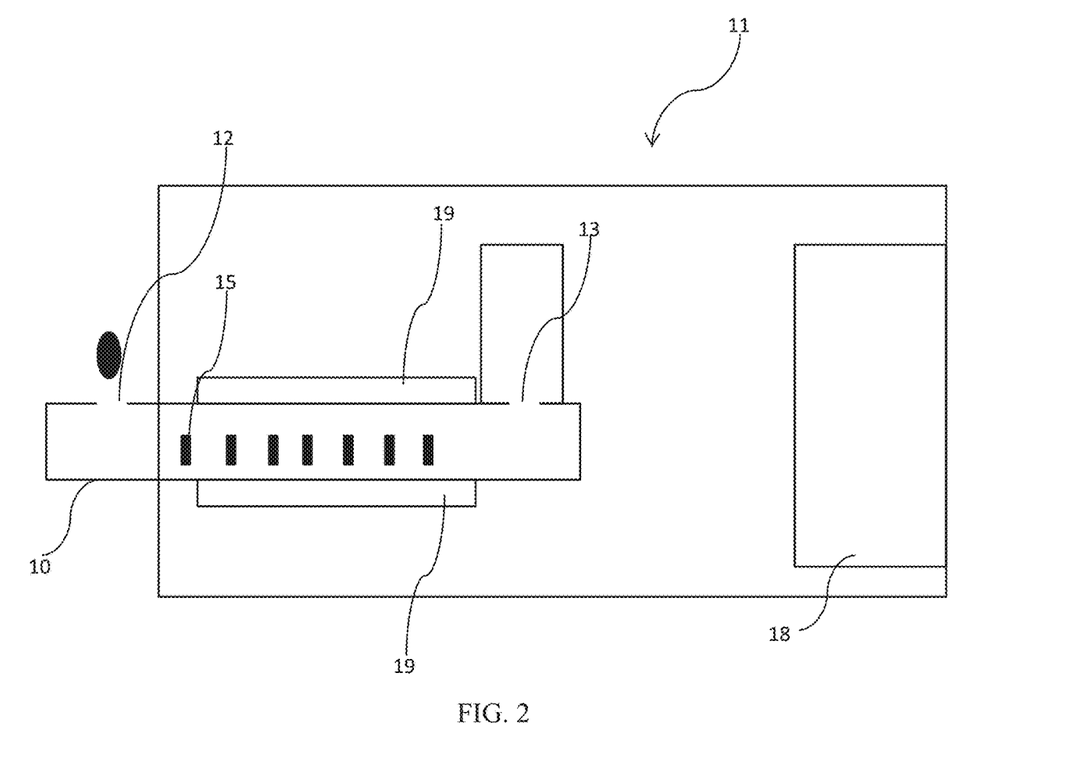
FIG. 2 is a more detailed view of the thromboelastography apparatus in accordance with this invention.

FIG. 2 shows a cross-sectional side view of the thromboelastography instrument (28) according to the invention. Blood is conveyed in the axial direction, from an inlet (12) to an outlet (13). Different embodiments of the invention have microfluidic channel (23) structures arranged for specific processes. Microfluidic channels (23) are formed through micro-pillar (15) arrangements. The heating units (19) are positioned on the top and bottom surface of the cartridge (10) to heat the cartridge (10) according to the input. Information about the input configuration will be explained in detail hereinafter.

Default settings for the heating units (19) to heat up cartridge (10) are preferably 37° C. which is generally accepted as average normal body temperature. Primary objective of the heating units (19) is to maintain constant temperature for the blood sample in the cartridge (10) along its length. For this purpose, heating units (19) extend along the microfluidic channels (23) through which the analysis is made.

Figure 3:
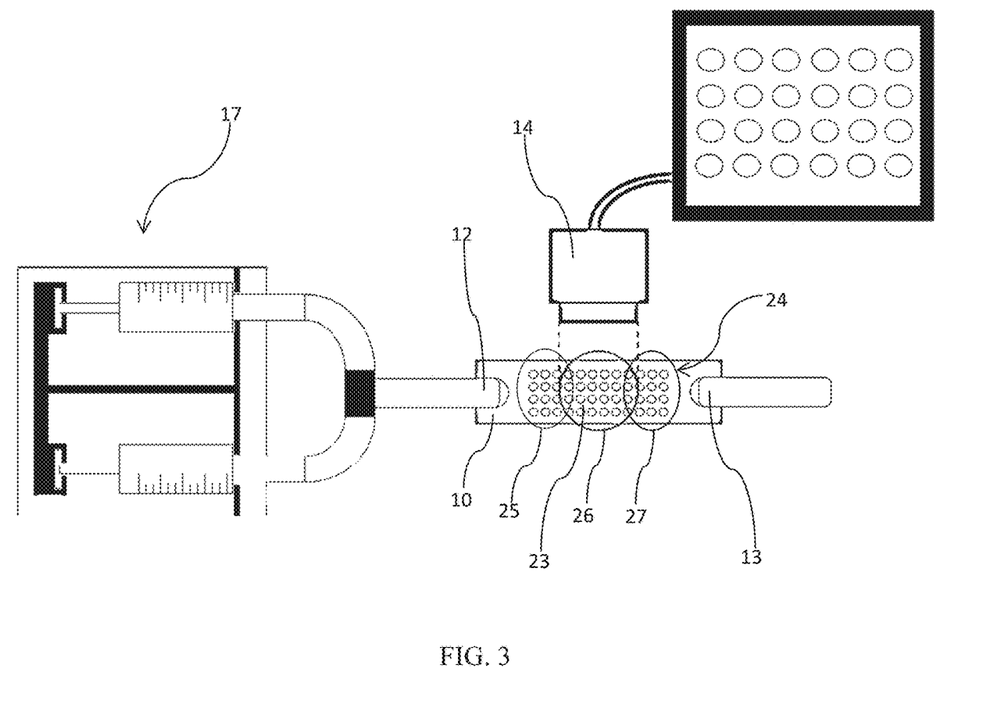
FIG. 3 is a top view of a thromboelastography apparatus in accordance with this invention.

FIG. 3 demonstrates a detailed top view of the thromboelastography instrument (28). The pumping unit (17) accelerates the coagulation cascade by allowing the blood sample injected into the cartridge (10) to move back and forth in the microfluidic channels (23). The cartridge (10) is equipped with the pumping unit (17) for displacement of the blood sample. In a variation, the cartridge may be connected to an external pumping unit (17) capable of then exerting a force on the blood sample to move the sample within the microfluidic channels (23). Alternatively, the pumping unit (17) can form an integral part of the cartridge (10). In another variation, a vacuum pump can be used to move the blood sample within the cartridge.

In accordance with the present invention, the blood sample moves in a micro-pillar matrix (24) which consists of plurality of micro-pillars (15). All of the micro-pillars (15) operate and act as mixing protrusions (16) despite the fact that particular ones among them may be employed to function for viscosity change measurement purposes. A maximum of 35 μL of blood sample from the patient is injected into the cartridge (10) without need of any preparation in any kind of sample retention structure. The amount of blood sample used in the cartridge (10) may preferably range from 10 to 30 μL. It is to be noted that one of the advantageous effects of the present invention is that the cartridge (10) unit does not need any other preparation container. Another advantageous effect of the present invention lies in that the system will only require 10-30 μL blood sample compared to 350 μL volume currently used in conventional TEG/TEM systems. The clot formation and fibrinolysis stages are carried out in the cartridge unit and the change in the viscoelastic properties of the blood is recorded by the measuring unit. The blood sample is moved back and forth in the microfluidic channels (23) formed by the micro-pillars (15) in the micro-pillar matrix (24) and interacts with the integrated elastic micro-pillars (15) present in the microfluidic channels (23) to apply force thereon.

In a further variation of the present invention, said micro-pillar matrix (24) comprises three different sections; a first micro-pillar field (25), a second micro-pillar field (26) and a third micro-pillar field (27). Some of the tests for coagulation analysis require addition of chemicals to the blood sample. The microfluidic channel (23) structures used in cartridges (10) according to the present invention, and particularly the first micro-pillar field (25), allow controlled mixing of the chemicals into the blood sample, thus ensuring that this type of analysis can be carried out with least possible amount of chemicals and with full homogenization with ease. For instance, a tissue factor (HTF. Human Thromboplastin Factor) should be added to the system which is a test equivalent to EXTEM. According to the present invention, the coagulation test can be performed by generating cartridges (10) with dried tissue factor (HTF) in the microfluidic channel (23) as a default configuration. It is also possible to apply different versions of the TEM analysis (INTEM, EXTEM, FIBTEM, HEPTEM, etc.) with cartridges (10) having the micro-pillar matrix (24) structure with different microfluidic channel (23) adjustments in parallel within the same instrument. Further, the first micro-pillar field (25) prepares blood sample flow for the analysis period by regulating the blood flow across the cartridges (10) to ensure that the transverse flow rate is the same in all microfluidic channels (23) through the second micro-pillar field (26). The specific diameters of the micro-pillars (15) on the micro-pillar matrix (24), the micro-pillar (15) lengths, the number of the micro-pillars (15) in the micro-pillar matrix (24), and the spacing between the micro-pillars (15) are specially adjusted to keep the mixture with said chemicals homogenized efficiently and blood flow rate constant. After the first micro-pillar field (25) regulates the blood flow, blood sample is transmitted to the second micro-pillar field (26). The second micro-pillar field (26) is the section where analysis is occurred. The imaging unit (14) monitors the micro-pillar (15) cluster in the second micro-pillar field (26) to gather information for assay. The imaging unit (14) comprises high speed camera to observe the displacement of the micro-pillar (15). In adverse circumstances, imaging unit (14) increases the optical visibility of the micro-pillars (15), for example by fluorescent marking; if the high speed camera module cannot operate at the desired speed, the camera is replaced by a secondary high-speed recording unit. The third micro-pillar field (27) serves in the same manner similar to the first micro-pillar field (25). It contributes to the regulation of the blood flow rate and the chemical mixing process while blood sample is moving back and forth.

Figure 4:
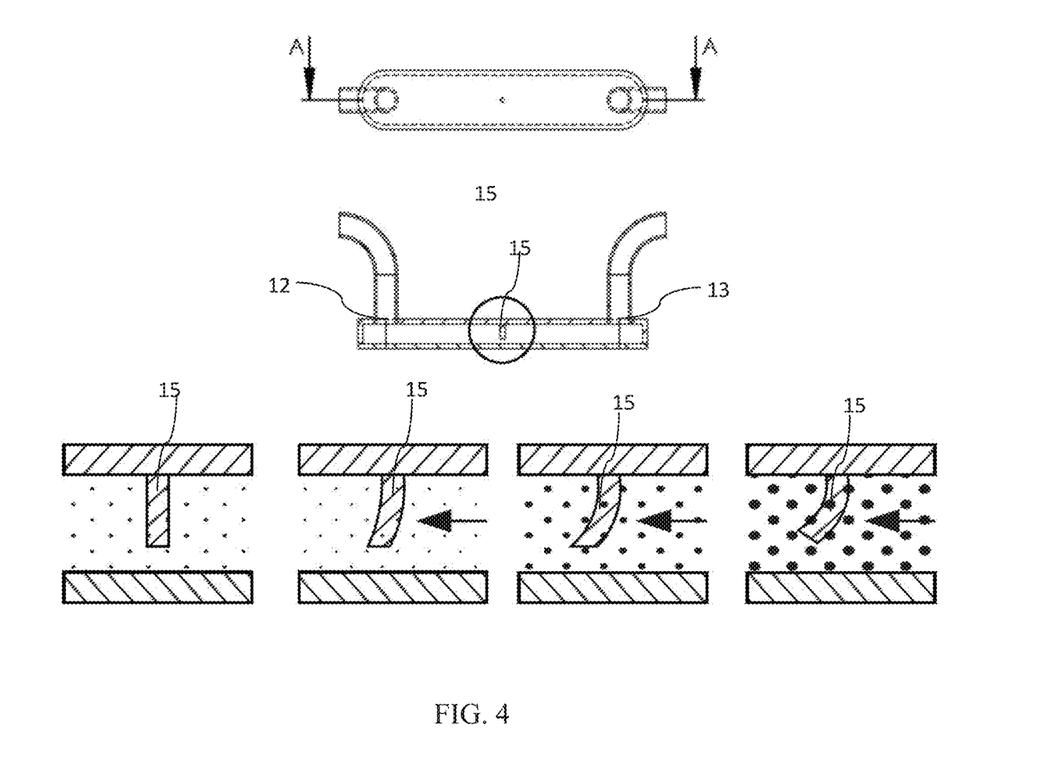
FIG. 4 is a cross sectional view taken along line A-A of the cartridge and detailed view of bending process of micro-pillar.
Figure 5:
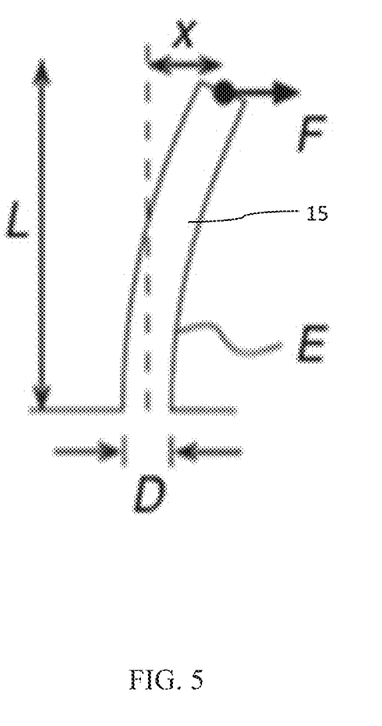
FIG. 5 is a general view of bended micro-pillar in accordance with this invention.

FIGS. 4-5 show bending process of micro-pillars (15). The force (F) applied to a micro-pillar (15) when the blood is moved in the microfluidic channel (23) is proportional to the viscoelastic properties of the blood and the change in these properties. The force (F) applied to micron-sized micro-pillars (15) can be approximated by the formula given below. The force (F) applied to the microstructure can be calculated by measuring the displacement (x) of the micro-pillars (15) using the imaging unit (14). The displacement (x) denotes the distance taken from the center of the micro-pillar (15) tip to the normal line taken from the center of the cross-section of the root thereof. By quantitative analysis of the deformation of the micro-pillars (15), the data obtained will be converted into tromboelastogram curves similar to the TEM and TEG graphs. In a typical TEM and TEG graph, the x-axis shows the time, while the y-axis shows the strength of the clot that is directly proportional to shaft displacement. The microstructural deformation (x) of the micro-pillars within the microfluidic channels (23) provides quantitative data directly proportional to clot strength/stiffness, similar to the motion of the spindle in the TEM and TEG curves. Parameters such as coagulation start time, coagulation time, time to reach maximum size of clot, stiffness and elasticity of clot, stability of clot and maximum lysis rate will be determined using coagulation curves obtained by the coagulation analysis system of the present invention. For instance, the coagulation start time is expressed by the CT parameter in the TEM and R parameter in the TEG curve and indicates the time to first fibrin bond formation. According to the present invention, at the moment the deformation (x) starts to increase, it will give an equivalent parameter to R or CT. Similarly, the slope of the rate of increase in the deformation will give a parameter equivalent to the clot formation rate "α".

$$F = k \times x$$

$$F = \frac{3\pi E D^4}{64 L^3} \times x$$

Figure 6:
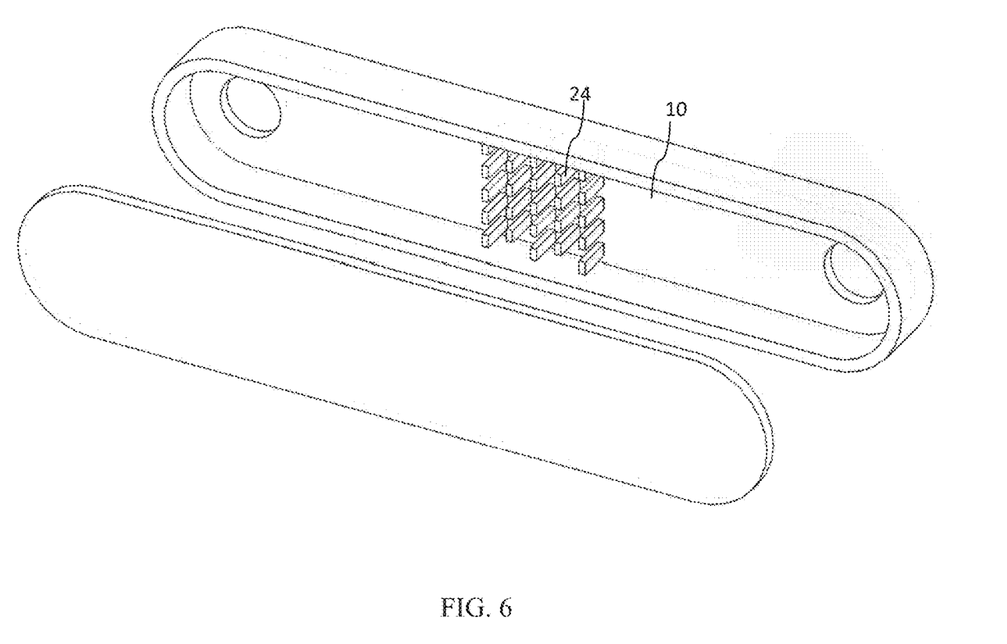
FIG. 6 is an embodiment in which the micro-pillars are provided in the form of a rectangular prism.
Figure 7:
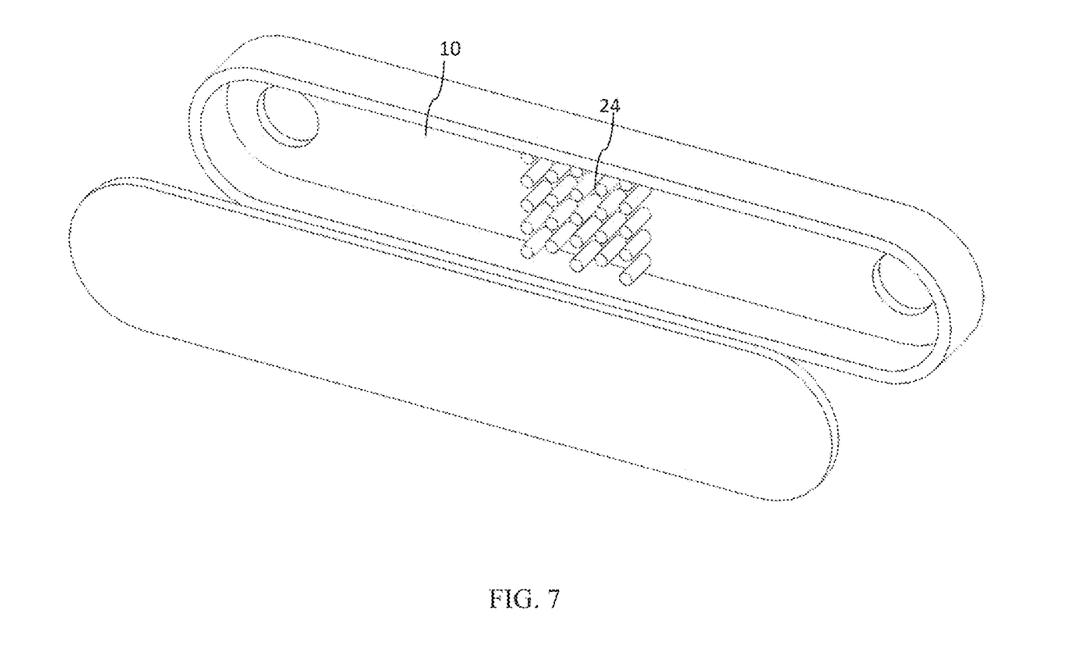
FIG. 7 is an embodiment in which the micro-pillars are provided in the form of a cylinder.
Figure 8:
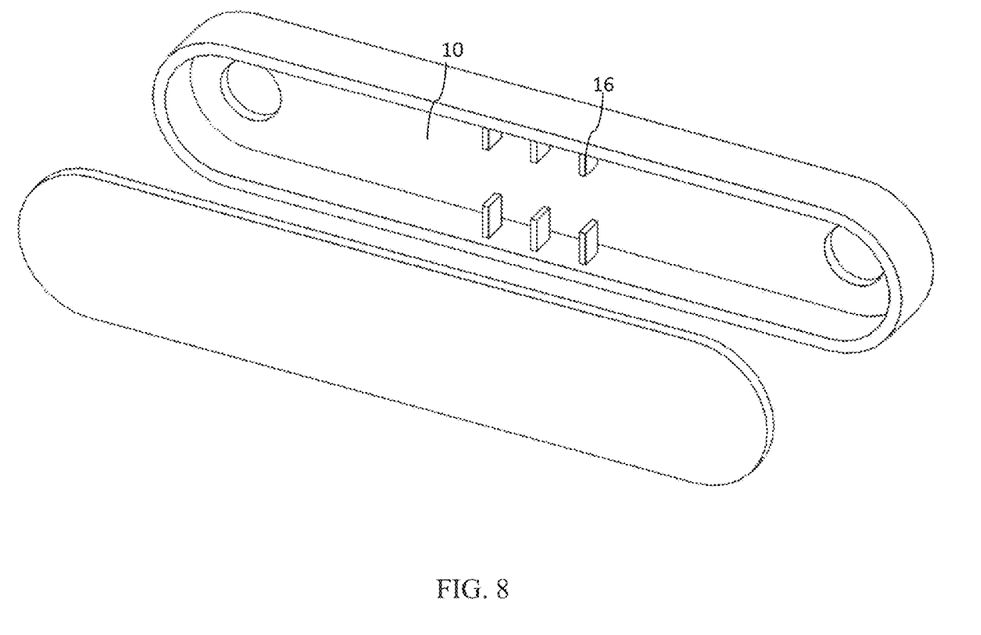
FIG. 8 is a perspective view of a cartridge consisting of mixing protrusions on the side walls.
Figure 9:
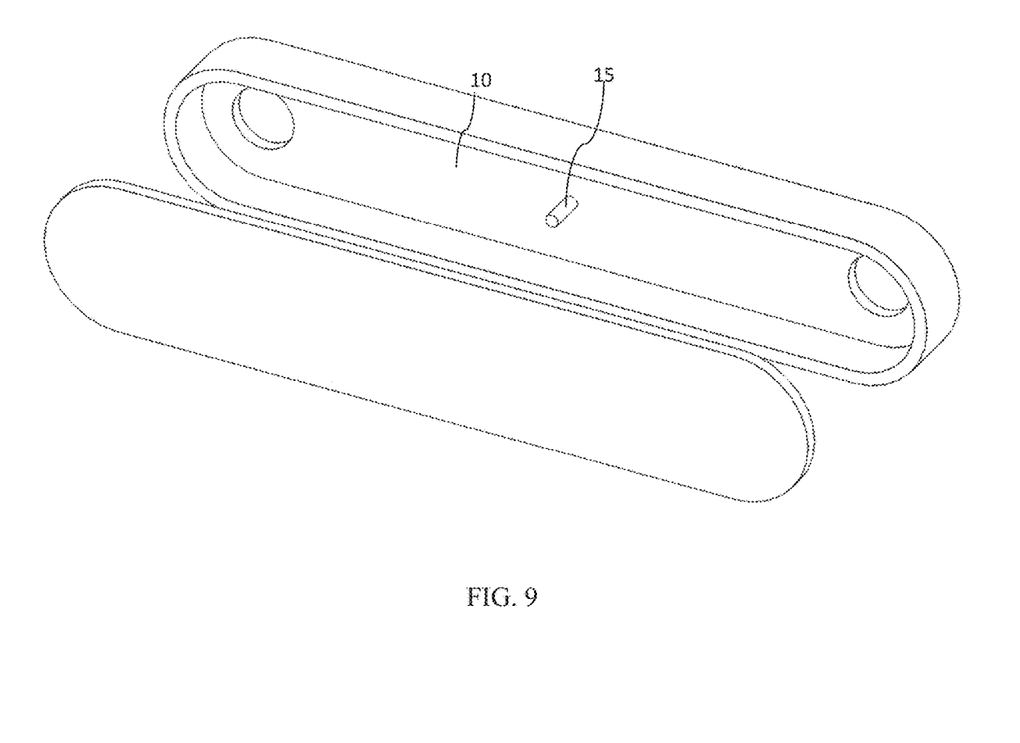
FIG. 9 is a perspective view of a cartridge consisting of a single micro-pillar.

FIGS. 6, 7, 8 and 9 show further variations of the present invention. FIG. 6 demonstrates an embodiment in which the micro-pillars (15) in the micro-pillar matrix (24) are provided in the form of a rectangular prism. FIG. 7 reconfigures above-mentioned embodiment in that the micro-pillars (15) in the micro-pillar matrix (24) are provided in the form of a cylinder. FIG. 8 shows mixing protrusions (16) used for the mixing procedure as located on the side walls of the cartridge (10). In this embodiment, the mixing protrusions (16) in the form of flaps placed on the side walls are adjusted so as to perform efficient deformation measurement on the micro-pillar (15) while mixing the necessary chemicals. Also, the mixing protrusions (16) on the sidewalls can be used in a similar fashion to micro-pillars (15) which are used for monitoring purposes. Viscosity changes can be monitored via analysis of deformations of the mixing protrusions (16) on the side walls. FIG. 9 shows an embodiment related to analysis with only one micro-pillar (15). In circumstances where the cartridge (10) or the microfluidic channel (23) is configured narrow enough, it is possible to make measurements with a single micro-pillar (15).

In a further variation of the present invention, necessary input to program the thromboelastography instrument (28) can be provided by scanning a barcode on the cartridge.

Once the patient's body temperature has been determined, the cartridge (10) will be inserted into the analyzing structure (11) and the heating units (19) will begin heating the cartridge (10) to the patient's body temperature. Further, the thromboelastography instrument (28) will specify the protocol to be used from the barcode on the cartridge (10), and the user will be instructed to add blood sample when the system is ready for testing. A drop of blood sample taken from the patient will be added to the cartridge (10) and the test will be started by drawing the sample into the microfluidic channels (23) with the aid of a pumping unit (17). Where the coagulation test requires the addition of a chemical to the blood, the chemical will be added in a lyophilized form to the microfluidic channels (23). When the blood is moved back and forth in the microfluidic channels (23), the deformation of the micro-pillars (15) will be examined and the time dependent change in the firmness of the clot will be shown on the screen (22). The screen (22) can be a touch screen to control the parameters manually. At the end of the test, the data obtained by the microcontroller (18) system can be converted into elastograms to be reported as test results and transmitted to the users (doctor, health personnel) through wireless data sharing.

In a further variation of the present invention, different chemicals can be added to different microfluidic channel (23) paths, therefore different tests can be performed within the same cartridge (10).

In another variation of the present invention, maximum size of the micro-pillars (15) is preferably provided in the diameter range of 30 μm, height of 80 μm and center to center spacing of 55 μm between any neighboring micro-pillar (15) pairs in the micro-pillar matrix (24).

In a further variation of the present invention, special chemicals and the necessary protocols will be automatically introduced to the cartridge (10) without specific input by the user. Further, the system is able to exchange wireless data using an ARM-based system such as Raspberry Pi. This reduces the duration of treatment of patient by ensuring that test results are communicated as soon as possible. Through this integration, chronic patient data can be continuously monitored and the trends in patient data can be used for diagnostic purposes. This reduces the duration of treatment of patient by ensuring that test results are communicated as soon as possible.

In another variation of the present invention, the cartridge (10) can be produced by means of soft lithography from transparent elastomer material called polydimethylsiloxane (PDMS). In the soft lithography method, a mold is first produced. The mold, which comprises the microfluidic channels (23) and the micro-pillars (15), is produced by a method such as microfabrication or 3D printing, then PDMS elastomer fluid is poured on it and it is allowed to crosslink and cure in the furnace or at room temperature. When the PDMS hardens, it takes the form of the micro-pillars (15) that are deposited on it. The PDMS layer containing these microstructures, separated from the mold, is activated with an oxygen plasma and sealed with a glass-like material and flow channels are formed. Although PDMS is not a frequently-used material in industry scale fabrication, it is widely used in microfluidic microchip production.

In a nutshell, the present invention proposes a thromboelastography instrument (28) that can work with much lower volume blood sample compared to traditional testing instruments, with a much lower cost of equipment and also allowing testing without the need for a trained staff to operate. 10-30 μL blood samples from the patient are sufficient for the system to operate. Clot formation and dissolution stages will take place in the cartridge (10) unit and the viscoelastic properties of the blood will be recorded by analyzing the structure (11). While blood sample is driven back and forth in channel, it will interact with integrated elastic micro-pillars (15). This interaction will be detected optically using imaging unit (14) and the force applied on micro-pillars (15) will be analyzed using special software algorithms. Subsequently the viscoelastic features of blood will be determined precisely by quantitative analysis.

In one embodiment of the present invention, the cartridge (10) for measuring changes in the viscosity of a fluid, the cartridge (10) comprising an inlet (12) and an outlet (13) between which flow of said fluid is provided through said cartridge (10).

In a further embodiment of the present invention, said cartridge (10) comprises at least one micro-pillar (15) having at least one first position, said micro-pillar (15) being capable of bending with the viscosity of the fluid increasing and restoring to its first position in response to viscosity decrease of said fluid.

In a further embodiment of the present invention, said micro-pillar (15) fixed to the surface of the cartridge (10) from the root and has a free distal extremity.

In a further embodiment of the present invention, displacement of the micro-pillar (15) distal extremity relative to the micro-pillar (15) root is monitored.

In a further embodiment of the present invention, plurality of micro-pillars (15) forms a micro-pillar matrix (24) that covers the cartridge (10) in transverse direction in the areas where the micro-pillars (15) exist.

In a further embodiment of the present invention, said micro-pillars (15) are equidistant from each other.

In a further embodiment of the present invention, said microfluidic channels (23) provide a linear path between the inlet (12) and the outlet (13).

In a further embodiment of the present invention, said microfluidic channels (23) provide a non-linear path between the inlet (12) and the outlet (13).

In a further embodiment of the present invention, said micro-pillar matrix (24) comprises a plurality of mixing protrusions (16) to operate as mixing bodies for chemicals and the fluid.

In a further embodiment of the present invention, said micro-pillar matrix (24) comprises a plurality of mixing protrusions (16) to operate as flow rate regulator.

In a further embodiment of the present invention, said micro-pillar matrix (24) comprises a plurality of micro-pillars (15) to be monitored for viscosity change analysis.

In a further embodiment of the present invention, said micro-pillar matrix (24) comprises a first micro-pillar field (25) providing homogenization as well as introducing fluid to said cartridge (10).

In a further embodiment of the present invention, said micro-pillar matrix (24) comprises a second micro-pillar field (26) which has a primary objective as to provide data for viscosity analysis through monitoring the displacement of micro-pillars (15).

In a further embodiment of the present invention, said micro-pillar matrix (24) comprises a third micro-pillar field (27) regulating blood flow rate and chemical mixing process to ensure accuracy of the monitoring process at said second micro-pillar field (26).

In a further embodiment of the present invention, the thromboelastography instrument (28) comprises said cartridge (10) and said analyzing structure (11).

In a further embodiment of the present invention, said analyzing structure (11) comprises a pumping unit (17) accelerating the viscosity change stage by moving the fluid injected into the cartridge back and forth through said microfluidic channels (23).

In a further embodiment of the present invention, said analyzing structure (11) has an imaging unit (14) which monitors at least one micro-pillar (15) to detect the displacement of said micro-pillar (15) distal extremity relative to the micro-pillar (15) root.

In a further embodiment of the present invention, said imaging unit (14) monitors said micro-pillar (15) cluster in the second micro-pillar field (26) to detect the displacement of said micro-pillar (15) distal extremity relative to the micro-pillar (15) root.

In a further embodiment of the present invention, said imaging unit (14) comprises high speed camera to observe the displacement of the micro-pillar (15).

In a further embodiment of the present invention, said analyzing structure (11) comprises heating units (19) to provide constant temperature values for the fluid in said cartridge (10).

In a further embodiment of the present invention, said heating units (19) are positioned on the top and bottom surface of the cartridge (10).

In a further embodiment of the present invention, said heating units (19) extend along the microfluidic channels (23).

In a further embodiment of the present invention, said heating units (19) are set to automatically heat up the fluid inside the cartridge (10) to 37° C.

In a further embodiment of the present invention, said analyzing structure (11) comprises a screen (22) which demonstrates information and allows user to give input to change parameters.

In a further embodiment of the present invention, said screen (22) is a touch screen.

In a further embodiment of the present invention, the maximum size of the micro-pillars (15) is provided in the diameter range of 30 µm, height of 80 µm and center to center spacing of 55 µm between micro-pillars (15) in the micro-pillar matrix (24).

In a further embodiment of the present invention, said microfluidic channels (23) structured to provide different chemicals on different microfluidic channel (23) paths, so as to allow different tests being performed within the same cartridge (10).

In a further embodiment of the present invention, said cartridge (10) is structured with a single micro-pillar (15), to make measurements on the same micro-pillar (15).

In a further embodiment of the present invention, at least one of the mixing protrusions (16) is located on the side walls of the cartridge (10).

In a further embodiment of the present invention, at least one of the micro-pillars (15) is located on the side walls of the cartridge (10).

In a further embodiment of the present invention, at least one of the micro-pillars (15) is provided in the form of a rectangular prism.

In a further embodiment of the present invention, at least one of the micro-pillars (15) is provided in the form of a cylinder.

A particular feature, structure, or characteristic described herein in connection with one embodiment may be implemented within other embodiments without departing from the scope of the invention. In addition, it is to be noted that the location or arrangement of individual elements within each disclosed embodiment may be modified without departing from the scope of the invention. The detailed description is, therefore, not to be taken in a limiting sense, and the scope of the present invention is defined only by the appended claims to be interpreted along with the full range of equivalents to which the claims are entitled.

What is claimed is:

1. A cartridge for measuring changes in a viscosity of a fluid, comprising an inlet and an outlet, wherein a flow of the fluid is provided through the cartridge between the inlet and the outlet, wherein
   the cartridge comprises at least one micro-pillar having at least one first position, the at least one micro-pillar is configured to bend with increasing of the flow and the viscosity of the fluid and to restore to the at least one first position of the at least one micro-pillar in response to decreasing of the viscosity of the fluid,
   the at least one micro-pillar is fixed to a surface of the cartridge from a root and the at least one micro-pillar has a free distal extremity,
   a displacement of the free distal extremity of the at least one micro-pillar relative to the root of the at least one micro-pillar is monitored.

2. The cartridge according to claim 1, wherein a plurality of micro-pillars forms a micro-pillar matrix, and the micro-pillar matrix covers the cartridge in a transverse direction in areas where the plurality of micro-pillars exist.

3. The cartridge according to claim 1, wherein a plurality of micro-pillars are positionally configured to create channel structures between the plurality of micro-pillars for a blood sample injected into the cartridge to move back and forth in microfluidic channels.

4. The cartridge according to claim 3, wherein the plurality of micro-pillars are equidistant from each other.

5. The cartridge according to claim 3, wherein the microfluidic channels provide a linear path between the inlet and the outlet.

6. The cartridge according to claim 3, wherein the microfluidic channels provide a non-linear path between the inlet and the outlet.

7. The cartridge according to claim 2, wherein the micro-pillar matrix comprises a plurality of mixing protrusions to operate as mixing bodies for chemicals and the fluid.

8. The cartridge according to claim 2, wherein the micro-pillar matrix comprises a plurality of mixing protrusions to operate as a flow rate regulator.

9. The cartridge according to claim 2, wherein the micro-pillar matrix comprises the plurality of micro-pillars to be monitored for a viscosity change analysis.

10. The cartridge according to claim 2, wherein the micro-pillar matrix comprises a first micro-pillar field providing homogenization as well as introducing the fluid to the cartridge.

11. The cartridge according to claim 2, wherein the micro-pillar matrix comprises a second micro-pillar field, wherein a primary objective of the micro-pillar matrix is configured to provide data for a viscosity analysis through monitoring the displacement of the free distal extremity of the at least one micro-pillar.

12. The cartridge according to claim 11, wherein the micro-pillar matrix comprises a third micro-pillar field regulating a blood flow rate and a chemical mixing process to ensure an accuracy of a monitoring process at the second micro-pillar field.

13. A thromboelastography instrument, comprising the cartridge according to claim 1 and an analysing structure, wherein the analyzing structure comprises a pumping unit, wherein the pumping unit accelerates a viscosity change stage by moving the fluid injected into the cartridge back and forth through microfluidic channels.

14. The thromboelastography instrument according to claim 13, wherein the analyzing structure comprises an imaging unit, wherein the imaging unit monitors the at least one micro-pillar to detect the displacement of the free distal extremity of the at least one micro-pillar relative to the root of the at least one micro-pillar.

15. The thromboelastography instrument according to claim 14, wherein the imaging unit monitors a micro-pillar cluster in a second micro-pillar field to detect the displacement of the free distal extremity of the at least one micro-pillar relative to the root of the at least one micro-pillar.

16. The thromboelastography instrument according to claim 14, wherein the imaging unit comprises a high speed camera to observe a displacement of the at least one micro-pillar.

17. The thromboelastography instrument according to claim 14, wherein the imaging unit increases an optical visibility of the at least one micro-pillar in an adverse circumstance by activating an extra light source.

18. The thromboelastography instrument according to claim 13, wherein the analyzing structure comprises heating units to provide constant temperature values for the fluid in the cartridge.

19. The thromboelastography instrument according to claim 18, wherein the heating units are positioned on a top surface of the cartridge and a bottom surface of the cartridge.

20. The thromboelastography instrument according to claim 18, wherein the heating units extend along the microfluidic channels.

21. The thromboelastography instrument according to claim 18, wherein the heating units are set to automatically heat up the fluid inside the cartridge to 37° C.

22. The thromboelastography instrument according to claim 13, wherein the analyzing structure comprises a light source, wherein a light intensity of the light source varies according to a viscosity change of the fluid.

23. The thromboelastography instrument according to claim 22, wherein the analyzing structure comprises a photo detector, wherein the photo detector detects the light intensity varying with the viscosity change of the fluid.

24. The thromboelastography instrument according to claim 13, wherein the analyzing structure comprises a screen, wherein the screen demonstrates information and the screen allows user to give an input to change parameters.

25. The thromboelastography instrument according to claim 24, wherein the screen is a touch screen.

26. The thromboelastography instrument according to claim 13, wherein a maximum size of a plurality of micro-pillars is provided in a diameter range of 30 μm, a height of 80 μm and a center to center spacing of 55 μm between the plurality of micro-pillars in a micro-pillar matrix.

27. The thromboelastography instrument according to claim 13, wherein the microfluidic channels are configured to provide different chemicals on different microfluidic channel paths to allow different tests being performed within a single cartridge.

28. The thromboelastography instrument according to claim 13, wherein the cartridge is configured to provide regulation of a blood flow with a single micro-pillar, to affect mixing with at least one chemical and to make measurements on the single micro-pillar.

29. The thromboelastography instrument according to claim 13, wherein at least one of a plurality of mixing protrusions is located on side walls of the cartridge.

30. The thromboelastography instrument according to claim 13, wherein at least one of a plurality of micro-pillars is located on side walls of the cartridge.

31. The thromboelastography instrument according to claim 13, wherein at least one of a plurality of micro-pillars is provided in a form of a rectangular prism.

32. The thromboelastography instrument according to claim 13, wherein at least one of a plurality of micro-pillars is provided in a form of a cylinder.

* * * * *